(12) United States Patent
Sato et al.

(10) Patent No.: US 11,540,998 B2
(45) Date of Patent: Jan. 3, 2023

(54) WATER-IN-OIL EMULSION COSMETIC

(71) Applicant: SHISEIDO COMPANY, LTD., Tokyo (JP)

(72) Inventors: Yukiko Sato, Yokohama (JP); Tomoko Ikeda, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 16/474,096

(22) PCT Filed: Dec. 13, 2017

(86) PCT No.: PCT/JP2017/044685
§ 371 (c)(1),
(2) Date: Jun. 27, 2019

(87) PCT Pub. No.: WO2018/123585
PCT Pub. Date: Jul. 5, 2018

(65) Prior Publication Data
US 2019/0321282 A1 Oct. 24, 2019

(30) Foreign Application Priority Data
Dec. 28, 2016 (JP) .............................. JP2016-256852

(51) Int. Cl.
| | |
|---|---|
| *A61K 8/894* | (2006.01) |
| *A61K 8/02* | (2006.01) |
| *A61K 8/06* | (2006.01) |
| *A61K 8/19* | (2006.01) |
| *A61K 8/29* | (2006.01) |
| *A61K 8/31* | (2006.01) |
| *A61K 8/34* | (2006.01) |
| *A61K 8/36* | (2006.01) |
| *A61K 8/37* | (2006.01) |
| *A61K 8/44* | (2006.01) |
| *A61K 8/73* | (2006.01) |
| *A61K 8/891* | (2006.01) |
| *A61Q 1/00* | (2006.01) |
| *A61Q 1/02* | (2006.01) |
| *A61Q 17/04* | (2006.01) |
| *A61Q 19/00* | (2006.01) |
| *A61Q 1/12* | (2006.01) |

(52) U.S. Cl.
CPC ............ *A61K 8/894* (2013.01); *A61K 8/0241* (2013.01); *A61K 8/062* (2013.01); *A61K 8/064* (2013.01); *A61K 8/19* (2013.01); *A61K 8/29* (2013.01); *A61K 8/31* (2013.01); *A61K 8/342* (2013.01); *A61K 8/361* (2013.01); *A61K 8/37* (2013.01); *A61K 8/375* (2013.01); *A61K 8/44* (2013.01); *A61K 8/445* (2013.01); *A61K 8/73* (2013.01); *A61K 8/732* (2013.01); *A61K 8/891* (2013.01); *A61Q 1/00* (2013.01); *A61Q 1/02* (2013.01); *A61Q 17/04* (2013.01); *A61Q 19/00* (2013.01); *A61K 2800/10* (2013.01); *A61K 2800/48* (2013.01); *A61K 2800/612* (2013.01); *A61K 2800/614* (2013.01); *A61K 2800/651* (2013.01); *A61Q 1/12* (2013.01)

(58) Field of Classification Search
None
See application file for complete search history.

(56) References Cited

U.S. PATENT DOCUMENTS

| | | | |
|---|---|---|---|
| 2006/0018858 A1 | 1/2006 | Chen et al. | |
| 2006/0024251 A1* | 2/2006 | Gardel | ................... A61K 8/064 424/63 |
| 2010/0166684 A1 | 7/2010 | Kokeguchi | |

(Continued)

FOREIGN PATENT DOCUMENTS

| | | |
|---|---|---|
| CN | 2009-155241 A | 7/2009 |
| CN | 105025866 A | 11/2015 |
| JP | 9-31358 | 2/1997 |
| JP | 3403223 | 5/2003 |
| JP | 2007-523199 | 8/2007 |

(Continued)

OTHER PUBLICATIONS

JPO English abstract for JP2009-155244 (Year: 2009).*

(Continued)

*Primary Examiner* — Sin J Lee
(74) *Attorney, Agent, or Firm* — Andrew F. Young; Nolte Lackenbach Siegel

(57) ABSTRACT

A low-viscosity water-in-oil cosmetic emulsion preparation gives a smooth use feeling, lightly spreads when applied, and has excellent dispersed-powder stability. The cosmetic emulsion preparation has (A) a polar oil which is liquid at 25° C. and has an IOB value exceeding 0.1, (B) a hydrocarbon oil, (C) a polyoxyalkylene; and alkyl-modified organopolysiloxane represented by general formula (I), and (D) a powder surface-treated with both an N-acylamino acid and methylpolysiloxane. (In formula (I), R represents a hydrogen atom or a C1-5 alkyl group, x is an integer of 5-50, y is an integer of 1-30, z is an integer of 20-200, a is an integer of 2-20, b is an integer of 1-5, c is an integer of 2-20, and d is an integer of 0-20).

(I)

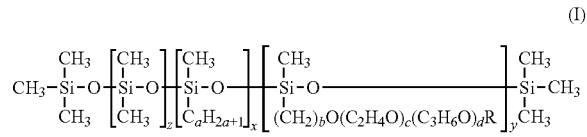

3 Claims, No Drawings

(56) References Cited

U.S. PATENT DOCUMENTS

| | | | | |
|---|---|---|---|---|
| 2010/0247458 A1* | 9/2010 | Kakoki | ............... | A61K 8/39 424/59 |
| 2011/0160312 A1* | 6/2011 | Oyama | ............... | A61K 8/042 514/784 |
| 2012/0277313 A1* | 11/2012 | Kwon | ............... | A61K 8/066 514/544 |
| 2014/0194522 A1* | 7/2014 | Kaizu | ............... | A61K 8/062 514/625 |

FOREIGN PATENT DOCUMENTS

| | | | | |
|---|---|---|---|---|
| JP | 2009-155241 A | 7/2009 | | |
| JP | 2009-155244 | 7/2009 | | |
| JP | 2009235046 A | * 10/2009 | ............ | A61K 8/891 |
| JP | 4373141 | 11/2009 | | |
| JP | 2013-079264 | 5/2013 | | |
| JP | 2013-253022 | 12/2013 | | |
| JP | 5791859 | 10/2015 | | |
| JP | 2016-190841 | 11/2016 | | |
| WO | WO2010/129313 A2 | 11/2000 | | |
| WO | WO 2011/010652 | 1/2011 | | |

OTHER PUBLICATIONS

Machine-assisted English translation for JP2009-155244 (Year: 2009).*
English abstract for WO 2011/010652 A1 (Year: 2011).*
English translation for TW 201117829 A1 (equivalent to WO 2011/010652 A1) (Year: 2011).*
JPO English abstract for JP2009-235046 (Year: 2009).*
Machine-assisted English translation for JP2009-235046 (Year: 2009).*
"Shiseida (Shisedo) anessa gold bottle 2014 edition" (English translation of product information sheet obtained at the website: https://www.cosdna.com/chs/cosmetic_1795137470.html (published on Mar. 23, 2014)) (Year: 2014).*
Shechter ("3 Differences Between Oil-in-Water & Water-in-Oil Emulsions", an internet article obtained at the website: https://www.beei.com/blog/3-differences-between-oil-in-water-water-in-oil-emulsions (published on Jul. 12, 2016)) (Year: 2016).*
Tan ("Review: Shiseido Anessa Perfect UV Sunscreen EX SPF50+ PA+++", an internet article obtained at the website: https://www.beei.com/blog/3-differences-between-oil-in-water-water-in-oil-emulsions (published on Mar. 29, 2013)) (Year: 2013).*
PCT/JP2017/044685, International Search Report (ISR) and Written Opinion (WO), dated Feb. 13, 2018, 4 pages—English, 8 pages—Japanese.
EP 17886811.3, Extended European Search Report dated Aug. 6, 2020, 9 pages—English.
Mintel, Deluxe Foundation, Babor Cosmetics, published Nov. 2018, http://www.gupd.com, 11 pages—English.
Organic Conception Diagram I Technology, 14 pages—English, nihon-emulsion.co.jp, dated Jul. 28, 2017, aboutreader?td=https://www.nihon-emulsion.cojp/en/tech/organic . . . .
Formulation Design with Organic Conception Diagram, Nihon Emulsion Co., Ltd,, published Nov. 1998, Revised on Mar. 26, 2001, 55 pages—English.
Shiseido anessa 2014, CosDNA, 3 pages—Chinese dated Dec. 6, 2021, 3 pages—English; https://www.cosdna.com/chs/cosmetic_1795137470.html.
CN 201780069439.1, Chinese Office Action dated Dec. 3, 2021, 8 pages—Chinese, 7 pages—English.

* cited by examiner

WATER-IN-OIL EMULSION COSMETIC

CROSS REFERENCE TO RELATED APPLICATIONS

This application relates to and claims priority as a § 371 national phase, from PCT/JP2017/044685 filed Dec. 13, 2017, the entire contents of which are incorporated herein by reference, which in turn claims priority to JP Ser. No. 2016-256852 filed on Dec. 28, 2016.

FIGURE SELECTED FOR PUBLICATION

None

TECHNICAL FIELD

The present invention relates to a water-in-oil emulsion cosmetic. More specifically, the present invention relates to a water-in-oil emulsion cosmetic, such as a cream foundation, that provides a user with a smooth feeling (sensation) in use and is lightly spreadable, and which has excellent powder dispersion stability.

BACKGROUND ART

A water-in-oil emulsion composition having an oil phase as the external phase and a water phase as the internal phase is able to efficiently extend (spread) oil-soluble active ingredients, such as emollient oils, oil-soluble medicinal agents and ultraviolet ray absorbing agents, on the skin, so that it is a suitable product form for an external skin preparation and therefore, is widely used for such as foundations and skin-care creams in the cosmetic field.

Conventional water-in-oil emulsion cosmetics are stabilized by gelling the oil constituting the external phase to immobilize water droplets and reduce the collision frequency between particles in many cases, so that the viscosity thereof tends inevitably to be higher. Therefore, it has been considered hard to achieve both reducing viscosity and increasing stability thereof at the same time with regard to water-in-oil emulsion cosmetics, and in addition, it has been difficult to improve spreadability and feeling in use when applied and over-time stability thereof all at the same time.

To date, various attempts have been made towards realizing a low-viscosity and stable water-in-oil emulsion cosmetic. For example, Patent Document 1 proposes to improve the stability over time of the emulsion state, the feeling in use and the texture by using a hydrophobic silica having a surface treated with a dimethylpolysiloxane as an emulsion stabilizer and using a specific silicone-based surfactant as an emulsifier.

Additionally, Patent Document 2 proposes a skin makeup composition in emulsion form, containing a non-emulsifying uncoated silicone elastomer, multiple N-acylamino acid-treated pigments, and an emulsifier. It teaches that the inclusion of the uncoated silicone elastomer stabilizes the emulsion, and the treatment of the pigments with N-acylamino acid, which is a non-silicone compound, makes it more unlikely for the pigments to re-aggregate during storage.

Furthermore, Patent Document 3 proposes using a mixture of an alkyl dimethicone polyol, a dimethicone copolyol, a hydrophobic coated pigment and a large amount of a volatile oil in order to obtain a foundation composition that provides excellent storage stability and allows uniform application for makeup of the skin.

However, the above-mentioned water-in-oil emulsion cosmetics use silicone oils as bases, and thus might have the problem of lacking smoothness and skin compatibility. Additionally, even if a hydrocarbon oil or a polar oil is added to these water-in-oil emulsion cosmetics in order to improve the feeling in use, sufficient improvements in smoothness may not be observed, and conversely, the stability may be worsen, and color stripes (irregularity) due to aggregation of pigments may occur.

RELATED ART

Patent Documents

Patent Document 1: JP 3403223 B
Patent Document 2: JP 5791859 B
Patent Document 3: JP 4373141 B

SUMMARY OF THE INVENTION

Problem to be Solved by the Invention

The present invention has been made in consideration of the above-mentioned drawbacks of the conventional art, and the purpose of the present invention is to provide a low-viscosity water-in-oil emulsion cosmetic that provides a user with a smooth feeling in use, is lightly spreadable when applied, and of which powder dispersion is excellently stable.

Means for Solving the Problem

Upon carrying out diligent research, the present inventors discovered that a low-viscosity water-in-oil emulsion cosmetic having excellent smoothness and good spreadability while retaining powder dispersion stability could be obtained by blending, as oil components, at least a polar oil and a hydrocarbon oil, and further blending a combination of a specific active agent and a powder that had been subjected to a specific surface treatment.

Specifically, the gist of the present invention is to provide a water-in-oil emulsion cosmetic comprising:
(A) a polar oil that is liquid at 25° C. and of which an IOB value is greater than 0.1;
(B) a hydrocarbon oil;
(C) a polyoxyalkylene/alkyl co-modified organopolysiloxane represented by a general formula (I) below:

[General formula I]

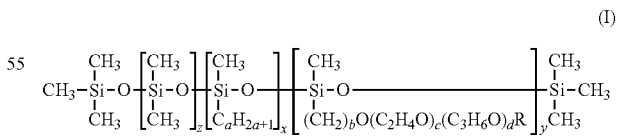

(I)

where R represents a hydrogen atom or an alkyl group having 1 to 5 carbon atoms, x represents an integer from 5 to 50, y represents an integer from 1 to 30, z represents an integer from 20 to 200, a represents an integer from 2 to 20, b represents an integer from 1 to 5, c represents an integer from 2 to 20, and d represents an integer from 0 to 20; and
(D) a powder of which surface is treated with an N-acylamino acid and a methylpolysiloxane.

Additionally, the water-in-oil emulsion cosmetic of the present invention preferably further comprises a thickener, and it is particularly preferable that the thickener is dextrin palmitate.

Effects of the Invention

According to the water-in-oil emulsion cosmetic of the present invention, such a cosmetic is feasible to provide a low viscosity while maintaining stability, so that such a cosmetic brings smoothness as if a skin-care cosmetic and a spreadable property and fresh feeling in use into reality. At the same time, such a cosmetic is excellent with regard to the stability of powder dispersion, so that the occurrence of color stripes due to the aggregation of powders can be prevented.

MODES FOR CARRYING OUT THE INVENTION

The water-in-oil emulsion cosmetic of the present invention comprises (A) a polar oil, (B) a hydrocarbon oil, (C) a polyoxylalkylene/alkyl co-modified organopolysiloxane, and (D) a surface-treated powder as essential components that characterize the cosmetic. Herebelow, the present invention will be explained in detail.

<(A) Polar Oil>

The (A) polar oil used in the water-in-oil emulsion cosmetic of the present invention is liquid at 25° C. and has an IOB value higher than 0.1, and particularly, it is preferable the IOB value is in the range of 0.1 to 0.5 is preferred.

The IOB, standing for Inorganic/Organic Balance, value is a value representing the ratio of the inorganic value to the organic value, and which serves as an indicator of the degree of polarity of an organic compound. The IOB value is specifically represented by: IOB value=inorganic value/organic value. Regarding the "inorganic value" and the "organic value" respectively, an "inorganic value" and an "organic value" are set for various types of atoms or functional groups so that, for example, the "organic value" is 20 for one carbon atom in a molecule and the "inorganic value" is 100 for one hydroxyl group. By summing the "inorganic values" and the "organic values" of all of the atoms and functional groups in an organic compound, it is possible to compute the LOB value of that organic compound (see, for example, Yoshio Koda, "*Yuki Gainenzu—Kiso to Oyo—*"[Organic Conceptual Diagrams—Fundamentals and Applications], pp. 11-17, published by Sankyo Shuppan, 1984).

Examples of polar oils satisfying such conditions include oleic acid (IOB value=0.42), isostearic acid (IOB value=0.43), isopropyl myristate (IOB value=0.18), octyl palmitate (IOB value=0.13), isopropyl palmitate (IOB value=0.16), butyl stearate (LOB value=0.14), hexyl laurate (IOB value=0.17), myristyl myristate (LOB value=0.11), decyl oleate (IOB value=0.11), isononyl isononanoate (IOB value=0.20), isotridecyl isononanoate (LOB value=0.15), cetyl ethylhexanoate (IOB value=0.13), glycol distearate (LOB value=0.16), glyceryl diisostearate (IOB value=0.29), neopentyl glycol dicaprate (IOB value=0.25), diisostearyl malate (LOB value=0.28), trimethylolpropane triisostearate (108 value=0.16), glyceryl tri-2-ethylhexanoate (triethylhexanoin) (IOB value=0.35), trimethylolpropane trioctanoate (IOB value=0.33), trimethylolpropane triisostearate (IOB value=0.16), diisobutyl adipate (IOB value=0.46), N-lauryol-L-glutamic acid -2-octyldodecyl ester (IOB value=0.29), 2-hexyldecyl adipate (IOB value=0.16), diisopropyl sebacate (IOB value=0.40), ethylhexyl methoxycinnamate (IOB value=0.28), olive oil (LOB value=0.16), castor oil (IOB value=0.43), decyltetradecanol (IOB value=0.21), octyldodecanol (IOB value=0.26), oleyl alcohol (IOB value=0.28) and the like.

The blended amount of the (A) polar oil should be 0.01 to 30% by mass, more preferably 0.1 to 20% by mass, and even more preferably 0.1 to 15% by mass relative to the overall amount of the water-in-oil emulsion cosmetic. If the blended amount of the (A) polar oil is less than 0.01% by mass, then a satisfactory feeling in use is hardly obtained, and if more than 30% by mass is blended, then the stability may be lost.

<(B) Hydrocarbon Oil>

(B) hydrocarbon oil used in the water-in-oil emulsion cosmetic of the present invention is generally known as a non-polar oil or a less-polar oil. Examples of hydrocarbon oils include liquid paraffin, isohexadecane, isododecane, ozokerite, squalane, squalene, pristane, paraffin, isoparaffin, ceresin, vaseline, microcrystalline wax, hydrogenated polyisobutene and the like.

The blended amount of the (B) hydrocarbon oil should be 0.01 to 30% by mass, more preferably 0.1 to 20% by mass, and even more preferably 0.1 to 10% by mass relative to the overall amount of the water-in-oil emulsion cosmetic. If the blended amount of the (B) hydrocarbon oil is less than 0.01% by mass, then a satisfactory feeling in use is hardly obtained, and if more than 30% by mass is blended, then it becomes undesirable in terms of the texture, such as it becoming more difficult to be spread on the skin. Additionally, it is preferable that the hydrocarbon oil is more than 0% by mass and up to 50% by mass, more preferably 5 to 40% by mass, or 10 to 30% by mass of the oil components. It is undesirable that the hydrocarbon oil content in the oil components is greater than 50% by mass in view of the texture, such as it is becoming harder to be spread on the skin.

<(C) Polyoxyalkylene/Alkyl Co-Modified Organopolysiloxane>

The (C) polyoxyalkylene/alkyl co-modified organopolysiloxane used in the water-in-oil emulsion cosmetic of the present invention is represented by the following general formula (I):

[General formula I]

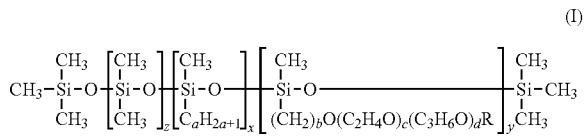

In general formula (I), R represents a hydrogen atom or an alkyl group having 1 to 5 carbon atoms, x represents an integer from 5 to 50, y represents an integer from 1 to 30, z represents an integer from 20 to 200, a represents an integer from 2 to 20, b represents an integer from 1 to 5, c represents an integer from 2 to 20, and d represents an integer from 0 to 20.

A preferable example of such a polyoxyalkylene/alkyl co-modified silicone is cetyl dimethicone copolyol (cetyl PEG/PPG-10/1 dimethicone) and as commercially available products, for example, KF-6048 (manufactured by Shin-etsu Chemical Co., Ltd.), ABIL EM 90 (manufactured by Degussa Japan Co., Ltd.) or the like can be used. Particularly, KF-6048 (manufactured by Shin-etsu Chemical Co., Ltd.) is preferred for providing extraordinaly excellent effects in terms of smoothness.

When (C) polyoxyalkylene/alkyl co-modified organopolysiloxane is applied in combination with the above-mentioned (A) polar oil and (B) hydrocarbon oil, the water-in-oil emulsion cosmetic having excellent smoothness can be obtained.

The blended amount of the (C) polyoxyalkylene/alkyl co-modified organopolysiloxane in the present invention should be 0.01 to 10% by mass, more preferably 0.01 to 5% by mass, and even more preferably 0.1 to 5% by mass relative to the overall amount of the water-in-oil emulsion cosmetic. If the blended amount is less than 0.01% by mass, the stability thereof tends to be lost. On the other hand, if the blended amount exceeds 10% by mass, the smooth feeling in use therefrom tends to be lost.

<(D) Powder Surface-Treated with N-Acylamino Acid and Methylpolysiloxane>

In the (D) powder of which surface is treated with an N-acylamino acid and a methylpolysiloxane (sometimes referred to simply as "surface-treated powder" in the present specification) used in the water-in-oil emulsion cosmetic of the present invention, the surface of the powder is coated with a layer comprising an N-acylamino acid and a layer comprising a methylpolysiloxane. The surface of the powder is coated with both N-acylamino acid and methylpolysiloxane, so that such a powder can be stably dispersed either in the (A) polar oil or the (B) hydrocarbon oil, resulting in that the formation of color stripes due to the aggregation of particles can be suppressed.

The powder as the core of the (D) surface-treated powder is not particularly restricted as long as it is normally used in cosmetics. Examples include inorganic white pigments (such as, for example, titanium dioxide and zinc oxide), inorganic red pigments (such as, for example, iron oxide (red iron oxide) and iron titanate), inorganic brown pigments (such as, for example, γ-iron oxide), inorganic yellow pigments (such as, for example, yellow iron oxide and ocher), inorganic black pigments (such as, for example, black iron oxide and lower titanium oxide), inorganic violet pigments (such as, for example, mango violet and cobalt violet), inorganic green pigments (such as, for example, chromium oxide, chromium hydroxide and cobalt titanate), inorganic blue pigments (such as, for example, ultramarine blue and Prussian blue), pearlescent pigments (such as, for example, titanium oxide-coated mica, titanium oxide-coated bismuth oxychloride, titanium oxide-coated talc, colored titanium oxide-coated mica, bismuth oxychloride and argentine) and metal powder pigments (such as, for example, aluminum powder and copper powder).

Additionally, an inorganic powder that is normally blended as an ultraviolet ray scattering agent in cosmetics can be used as the core. When such an ultraviolet ray scattering agent is used as the core, ultraviolet ray protection effects to the water-in-oil emulsion cosmetic of the present invention can be imparted. Examples of ultraviolet ray scattering agents that can serve as cores include fine-particle titanium oxide and fine-particle zinc oxide having an average primary particle size of 10 nm to 100 nm, more preferably 10 nm to 50 nm.

The N-acylamino acid coating the surface of the powder is the amino acid in which an amino group and/or an imino group is acylated, or a salt thereof. Examples of the N-acylamino acid include N-stearoyl-L-glutamic acid, N-lauroyl-L-lysine and the like, and examples of salts include sodium salts, potassium salts and triethanolamine salts.

Additionally, methylpolysiloxane, having a degree of polymerization of approximately 10 to 100, is preferably used in order to provide sufficient dispersion properties in the powder.

The (D) surface-treated powders that can be used in the present invention may be produced, for example, by means of the method disclosed in JP 2001-72527 A. As commercially available products, for example, SA/NAI-CR-50P, SANAI-R-516P, SA/NAI-LL-100P or SA/NAI-BL-100P (all manufactured by Miyoshi Kasei, Inc.) can be used.

The blended amount of the (D) surface-treated powder in the present invention should be 1 to 50% by mass, more preferably 5 to 30% by mass, and even more preferably 5 to 20% by mass relative to the overall amount of the water-in-oil emulsion cosmetic. If the blended amount of the (D) surface-treated powder is less than 1% by mass relative to the cosmetic, satisfactory cosmetic effects can be hardly obtained, and if the amount exceeds 50% by mass, any detrimental impact on the texture, such as the occurrence of coarseness or the like, tends to take place.

<Other Ingredients>

In the water-in-oil emulsion cosmetic of the present invention, aside from the above-mentioned ingredients, other ingredients that are normally used in cosmetics such as various types of aqueous solvents, oil components, thickeners, oil components other than the above, powder ingredients, surfactants, metal ion sequestering agents, sugars, amino acids, organic amines, pH adjusters, ultraviolet ray scattering agents, ultraviolet ray absorbing agents, skin nutrients, vitamins, antioxidants, antioxidant aids, fragrances, can be used as needed within a range not compromising the effects of the present invention.

Aqueous Solvent

As an aqueous solvent, water (ion-exchanged water, purified water, natural water or the like), or an aqueous ingredient such as a lower alcohol or a polyhydric alcohol can be formulated within a range not compromising the stability of the cosmetic.

Oil Component

The water-in-oil emulsion cosmetic of the present invention may contain oil components other than the above-mentioned (A) polar oil and (B) hydrocarbon oil, as long as the effects of the present invention are not compromised. In particular, a fresh feeling in use, oil resistance and water resistance can be obtained by blending a silicone oil. Examples of silicone oils that may be blended include organopolysiloxanes such as dimethyl polysiloxanes, methyl hydrogen polysiloxanes, methyl phenyl polysiloxanes, methyl polycyclosiloxanes, alkyl-modified silicones, amino-modified silicones, epoxy-modified silicones, carboxyl-modified silicones, chloroalkyl-modified silicones, alkyl higher alcohol ester-modified silicones, alcohol-modified silicones, polyether-modified silicones, fluorine-modified silicones and the like. Of these silicone oils, methyl polycyclosiloxane (cyclomethicone) is preferred for safety and the feeling in use on the skin, as well as the availability at the current time.

Thickener

The water-in-oil emulsion cosmetic of the present invention preferably contains a thickener for improving the stability. However, if an organically modified clay mineral such as dimethyl distearyl ammonium hectorite, which is commonly used in conventional water-in-oil foundations, is blended, there is a tendency for the smoothness to be lost and the cosmetic to become difficult to be spread. In the water-in-oil emulsion cosmetic of the present invention, it is known that excellent smoothness and spreadability can be realized by blending, as the thickener, in particular, dextrin palmitate (e.g., Rheopearl KL (manufactured by Chiba Flour Milling Co., Ltd.)), glyceryl (behenate/eicosadioate) (e.g., Nomcort HK-G (manufactured by Nisshin OilliO Group, Ltd.)), polyglyceryl-10 (behenate/eicosadioate) (e.g., Nomcort HK-P (manufactured by Nisshin OilliO Group, Ltd.)), sucrose fatty acid esters such as sucrose acetate/stearate and sucrose stearate, dibutyl lauroyl glutamide (e.g., GP-1 (manufactured by Ajinomoto Co., Inc.)) dibutyl ethylhexanoyl glutamide (e.g., EB-21 (manufactured by Ajinomoto Co., Inc.)), polyamide resins such as polyamide-8, and hydroxystearic acid (e.g., 12-hydroxystearic acid (manufactured by Kawaken Fine Chemicals Co., Ltd.)).

When blending a thickener, it is preferable that the amount thereof is 0.01 to 10% by mass, more preferably 0.01 to 5% by mass, and even more preferably 0.1 to 1% by mass relative to the overall amount of the water-in-oil emulsion cosmetic.

Spherical Resin Powder

The water-in-oil emulsion cosmetic of the present invention preferably contains a spherical resin powder that is normally used in cosmetic products in order to improve the feeling in use. Examples of spherical resin powders that may be used include polyamide resins (nylon powders), polyethylene powders, poly methyl methacrylate powders, polyurethane powders, polystyrene powders, poly alkyl acrylate powders, styrene/acrylic acid copolymer resin powders, silicone powders, crosslinked silicone powders and the like.

Ultraviolet Ray Scattering Agent

The water-in-oil emulsion cosmetic of the present invention may contain an ultraviolet ray scattering agent for the purpose of imparting or improving the ultraviolet ray protection effects. Although the ultraviolet ray scattering agent used in the present invention is not particularly limited, for example, fine-particle titanium oxide and fine-particle zinc oxide, having an average primary particle size of 10 nm to 100 nm and more preferably 10 nm to 50 nm, can be used. Additionally, the ultraviolet ray scattering agent may be hydrophobically treated by a publicly known method, and examples of the hydrophobic treatment method include, for example, treatments using silicones such as methyl hydrogen polysiloxane, methyl hydrogen polysiloxane/dimethylpolysiloxane copolymers, and dimethylpolysiloxane; treatments using silane compounds such as octyltriethoxysilane and hexyltrimethoxysilane; treatments using fatty acids such as palmitic acid and stearic acid; metal soap treatments using alkali metal salts or alkaline earth metal salts of the aforementioned fatty acids; and fluorine treatments such as diethanolamine salts of perfluoroalkyl phosphoric acid and perfuoroalkyl trimethoxysilane.

Ultraviolet Ray Absorbing Agent

The water-in-oil emulsion cosmetic of the present invention may contain an ultraviolet ray absorbing agent for imparting or improving the ultraviolet ray protection effects. Although the ultraviolet ray absorbing agent is not particularly limited, for example, benzoic acid derivatives, salicylic acid derivatives, cinnamic acid derivatives, dibenzoylmethane derivatives, β,β-diphenyl acrylate derivatives, benzophenone derivatives, benzylidene camphor derivatives, phenylbenzoimidazole derivatives, triazine derivatives, phenylbenzotriazole derivatives, anthranil derivatives, imidazoline derivatives, benzalmalonate derivatives, 4,4-diaryl butadiene derivatives and the like. More specific examples include organic ultraviolet ray absorbing agents such as ethylhexyl methoxycinnamate, octocrylene, polysilicone-15, t-butyl methoxydibenzoyl methane, ethylhexyl triazone, diethylamino hydroxybenzoyl hexyl benzoate, bis-ethylhexyloxyphenol methoxyphenyl triazine, oxybenzone-3, methylene bis-benzotriazolyl tetramethylbutylphenol, phenylbenzimidazole sulfonic acid, homosalate, ethylhexyl salicylate and 2-hydroxy-4-methoxybenzophenone, can be used.

The water-in-oil emulsion cosmetic of the present invention can be prepared by a conventional method, and the method of emulsification is not particularly limited. For example, a method of heating both the water phase and the oil phase to approximately 70° C., gradually adding the heated water phase to the oil phase, emulsifying with an emulsifier, then allowing to cool to room temperature may be mentioned, but the method is not limited thereto.

The water-in-oil emulsion cosmetic of the present invention can be applied to a wide range of cosmetics, and for example, may be an emulsion foundation, a sun-care cosmetic, a makeup base or the like.

Additionally, the present invention is not limited in terms of the form of the container. For example, an impregnated body may be impregnated with this cosmetic and housed in a compact container that is airtight. Examples of the impregnated body include non-woven fabrics comprising single or mixed materials such as resins, pulp, cotton or the like, resin treated fiber bodies, foamed bodies such as sponges, and porous bodies comprising continuous pores. Additionally, examples of the material of the impregnated body include NBR (acrylonitrile butadiene rubber), SBR (styrene butadiene rubber), NR (natural rubber), urethane, nylon, polyolefin, polyester, EVA (ethylene vinyl acetate), PVA (polyvinyl alcohol), silicone, elastomers and the like. However, the material is not limited to these as long as the impregnated body is able to contain a cosmetic.

EXAMPLES

Herebelow, the present invention will be explained in further detail by giving examples, but the present invention is not limited by these examples. The blended amounts are indicated in % by mass where not particularly noted otherwise. Prior to describing the examples, the evaluation method used in the present invention will be explained.

(I) Smoothness and Spreadability (Lightly Spreadable)

Actual application tests were performed by 10 expert panelists on each of the samples. Specifically, emulsion foundations according to the respective samples were applied to the face of each panelist, and the smoothness and spreadability were evaluated in accordance with the following criteria.

<Evaluation Criteria>

A: 7 or more out of 10 evaluated the sample as being excellent

B: 5 or more and less than 7 out of 10 evaluated the sample as being excellent

C: Less than 5 out of 10 evaluated the sample as being excellent (2) Color Stripes (Powder Dispersion Properties)

Transparent glass containers were filled with the respective samples, and after allowing to stand for 1 hour, the formation of stripes caused by unevenness of the powder was evaluated by visual observation.

A: Absolutely no stripe patterns were observed

B: Some stripe patterns were observed, but within an acceptable level

C: Stripe patterns were observed and unacceptable for use as a cosmetic

The emulsion foundations indicated in Tables 1 and 2 below were prepared, and the respective properties were evaluated in accordance with the above-described evaluation methods. The results are also shown in Tables 1 and 2.

TABLE 1

|  | Example 1 | Example 2 | Example 3 | Example 4 | Example 5 |
|---|---|---|---|---|---|
| Cetyl dimethicone copolyol *[1] | 3 | 1 | 5 | 3 | 3 |
| Polyether-modified silicone | 0.5 | 2 | 0.1 | 0.5 | 0.1 |
| Isohexadecane | 3 | 5 | 2 | — | — |
| Squalane | 5 | 10 | 2 | 8 | 10 |
| Triethylhexanoin | 3 | 2 | 10 | 3 | — |
| Cetyl ethylhexanoate | 5 | 2 | 10 | 10 | 15 |
| Ethylhexyl methoxycinnamate | 4 | 4 | 4 | — | — |
| Cyclomethicone | 5 | 5 | 5 | 5 | 10 |
| Dextrin palmitate *[2] | 0.5 | 1 | 2 | 0.5 | 0.5 |
| Surface-treated powder A *[3] | 12 | 20 | 25 | 12 | 12 |
| Polymethylmethacrylate | 2 | 2 | 2 | 2 | 2 |
| Dipropylene glycol | 5 | 5 | 5 | 5 | 5 |
| Glycerin | 5 | 5 | 5 | 5 | 5 |
| Water | balance | balance | balance | balance | balance |
| Smoothness | A | B | B | A | B |
| Spreadability | B | B | B | B | B |
| Color stripes | B | B | B | B | B |

TABLE 2

|  | Comp. Example 1 | Comp. Example 2 | Comp. Example 3 | Comp. Example 4 | Comp. Example 5 |
|---|---|---|---|---|---|
| Cetyl dimethicone copolyol *[1] | — | 3 | 3 | 3 | 3 |
| Polyether-modified silicone | 2 | 0.5 | 0.5 | 0.5 | 0.5 |
| Isohexadecane | 3 | — | 3 | 3 | 3 |
| Squalane | 5 | — | 5 | 5 | 5 |
| Triethylhexanoin | 3 | 3 | — | 3 | 3 |
| Cetyl ethylhexanoate | 5 | 5 | — | 5 | 5 |
| Ethylhexyl methoxycinnamate | 4 | 4 | — | 4 | 4 |
| Cyclomethicone | 5 | 20 | 25 | 5 | 5 |
| Dextrin palmitate *[2] | 0.5 | 0.5 | 0.5 | 0.5 | 0.5 |
| Surface-treated powder A *[3] | 12 | 12 | 12 | — | — |
| Surface-treated powder B *[4] | — | — | — | 12 | — |
| Surface-treated powder C *[5] | — | — | — | — | 12 |
| Polymethylmethacrylate | 2 | 2 | 2 | 2 | 2 |
| Dipropylene glycol | 5 | 5 | 5 | 5 | 5 |
| Glycerin | 5 | 5 | 5 | 5 | 5 |
| Water | balance | balance | balance | balance | balance |
| Smoothness | C | C | C | C | C |
| Spreadability | B | C | B | C | B |
| Color stripes | B | B | B | C | C |

*[1]) KF-6048 (manufactured by Shin-etsu Chemical Co., Ltd.)

*[2]) Rheopearl KL (manufactured by Chiba Flour Milling Co., Ltd.)

*[3]) Surface-treated powder obtained by treating the surface of raw material powder, having following composition, with N-acylamino acid and methylpolysiloxane:

Titanium oxide 80%

Red iron oxide 4%

Yellow iron oxide 15%

Black iron oxide 1%

*[4]) Surface-treated powder obtained by treating the surface of the raw material powder, having following composition, with triethoxycaprylyl silane:

Titanium oxide 80%

Red iron oxide 4%

Yellow iron oxide 15%

Black iron oxide 1%

*[5]) Surface-treated powder obtained by treating the surface of raw material powder having following composition with perfluorooctylethyl trimethoxysilane and dimethicone:

Titanium oxide 80%

Red iron oxide 4%

Yellow iron oxide 15%

Black iron oxide 1%

As indicated in Table 1, when (A) a polar oil, (B) a hydrocarbon oil, (C) a polyoxyalkylene/alkyl co-modified organopolysiloxane, and (D) a surface-treated powder were blended, satisfactory effects were obtained with regard to all evaluation categories (Examples 1 to 5). In contrast therewith, as shown in Table 2, when any one of (A) to (D) was not formulated, the smoothness or spreadability became worse (Comparative Examples 1 to 3). Furthermore, when a powder other than (D) was blended, the formation of color stripes exceeding the tolerable limit was observed (Comparative Examples 4 and 5).

Formulation Examples

Herebelow, formulation examples of the water-in-oil emulsion cosmetic of the present invention will be described. Needless to say, the present invention is not limited in any way by these formulation examples and defined by the claims. The blended amounts are all indicated in % by mass relative to the overall amount of the product.

Formulation Example 1 (Makeup Base)

| (Ingredient) | Blended amount (%) |
|---|---|
| (1) Cetyl dimethicone copolyol *[6] | 3 |
| (2) Polyether-modified silicone | 0.5 |
| (3) Isododecane | 5 |
| (4) Cetyl ethylhexanoate | 5 |
| (5) Ethylhexyl methoxycinnamate | 5 |
| (6) Cyclomethicone | 10 |
| (7) Dextrin palmitate *[2] | 0.5 |
| (8) Surface-treated powder A *[3] | 5 |
| (9) Polymethylmethacrylate | 10 |
| (10) Dipropylene glycol | 5 |
| (11) Glycerin | 1 |
| (12) Water | balance |

*[6]) ABIL EM 90 (manufactured by Degussa Japan Co., Ltd.)

Production Method (1) to (7) were homogeneously mixed while heating to prepare an oil phase portion, and powder portions (8) and (9) were dispersed in the oil phase portion to make a mixture. Next, (10) to (12) were melted by heating to prepare a water phase portion, which was added and mixed into the aforementioned mixture to make a makeup base.

Formulation Example 2 (Makeup Base)

| (Ingredient) | Blended amount (%) |
| --- | --- |
| (1) Cetyl dimethicone copolyol *6) | 3 |
| (2) Polyether-modified silicone | 1 |
| (3) Isododecane | 5 |
| (4) Trimethylsiloxy cinnamic acid | 5 |
| (5) Ethylhexyl methoxycinnamate | 8 |
| (6) Polysilicone-15 | 2 |
| (7) bis-Ethylhexyloxyphenol methoxyphenyl triazine | 1 |
| (8) t-Butyl methoxydibenzoyl methane | 1 |
| (9) Ethylhexyl triazone | 0.5 |
| (10) Cyclomethicone | 10 |
| (11) Dextrin palmitate *2) | 0.5 |
| (12) Titanium oxide surface-treated with N-acylamino aci and methylpolysiloxane | 1 |
| (13) Spherical polyurethane resin | 10 |
| (14) Dipropylene glycol | 5 |
| (15) Glycerin | 1 |
| (16) Water | balance |

Production Method (1) to (11) were homogeneously mixed while heating to prepare an oil phase portion, and powder portions (12) and (13) were dispersed in the oil phase portion to make a mixture. Next, (14) to (16) were melted by heating to prepare a water phase portion, which was added and mixed into the aforementioned mixture to make a makeup base.

Formulation Example 3 (Makeup Base)

| (Ingredient) | Blended amount (%) |
| --- | --- |
| (1) Cetyl dimethicone copolyol *6) | 3 |
| (2) Polyether-modified silicone | 1 |
| (3) Isododecane | 5 |
| (4) Trimethylsiloxy silicic acid | 5 |
| (5) Ethylhexyl methoxycinnamate | 8 |
| (6) Diethylamino hydroxybenzoyl hexyl benzoate | 1 |
| (7) 2-hydroxy-4-methoxybenzophenone | 1 |
| (8) Cyclomethicone | 10 |
| (9) Dextrin palmitate *2) | 0.5 |
| (10) Titanium oxide surface-treated with N-acylamino acid and methylpolysiloxane | 1 |
| (11) Spherical polyurethane resin | 10 |
| (12) Phenylbenzimidazole sulfonic acid | 1 |
| (13) Triethenolamine | s.a. |
| (14) Dipropylene glycol | 5 |
| (15) Glycerin | 1 |
| (16) Water | balance |

Production Method (1) to (9) were homogeneously mixed while heating to prepare an oil phase portion, and powder portions (10) and (11) were dispersed in the oil phase portion to make a mixture. Next, (12) to (16) were melted by heating to prepare a water phase portion, which was added and mixed into the aforementioned mixture to make a makeup base.

Formulation Example 4 (Sunscreen)

| (Ingredient) | Blended amount (%) |
| --- | --- |
| (1) Cetyl dimethicone copolyol *6) | 3 |
| (2) Polyether-modified silicone | 1 |
| (3) Isododecane | 5 |
| (4) Trimethylsiloxy silicic acid | 5 |
| (5) Ethylhexyl methoxycinnamate | 8 |
| (6) Cyclomethicone | 10 |
| (7) Dextrin palmitate *2) | 0.5 |
| (8) Titanium oxide surface-treated with N-acylamino acid and methylpolysiloxane | 1 |
| (9) Spherical polyurethane resin | 10 |
| (10) Dipropylene glycol | 5 |
| (11) Glycerin | 1 |
| (12) Water | balance |

Production Method (1) to (7) were homogeneously mixed while heating to prepare an oil phase portion, and powder portions (8) and (9) were dispersed in the oil phase portion to make a mixture. Next, (10) to (12) were melted by heating to prepare a water phase portion, which was added and mixed into the aforementioned mixture to make a sunscreen.

Formulation Example 5 (Foundation)

| (Ingredient) | Blended amount (%) |
| --- | --- |
| (1) Cetyl dimethicone copolyol *6) | 3 |
| (2) Polyether-modified silicone | 0.5 |
| (3) Isododecane | 5 |
| (4) Cetyl ethylhexanoate | 5 |
| (5) Ethylhexyl methoxycinnamate | 5 |
| (6) Cyclomethicone | 10 |
| (7) Dibutyl lauroyl glutamide *7) | 0.2 |
| (8) Surface-treated powder A *3) | 15 |
| (9) Silica | 5 |
| (10) Dipropylene glycol | 5 |
| (11) Glycerin | 1 |
| (12) Water | balance |

*7) GP-1 (Ajinomoto Co., Inc.)

(1) to (7) were homogeneously mixed while heating to prepare an oil phase portion, and powder portions (8) and (9) were dispersed in the oil phase portion to make a mixture. Next, (10) to (12) were melted by heating to prepare a water phase portion, which was added and mixed into the aforementioned mixture to make a foundation.

The invention claimed is:

1. A water-in-oil emulsion cosmetic, comprising:
   (A) 8-24% by mass of a polar oil that is liquid at 25° C. and having an IOB value greater than 0.1;
   (B) 0.1 to 10% by mass of a hydrocarbon oil;
   (C) a polyoxyalkylene/alkyl co-modified organopolysiloxane represented by general formula (I) below:

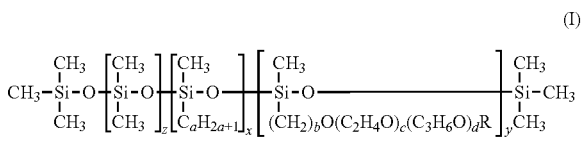

(I)

where R represents a hydrogen atom or an alkyl group having 1 to 5 carbon atoms, x represents an integer from 5 to 50, y represents an integer from 1 to 30, z represents an integer from 20 to 200, a represents an integer from 2 to 20, b represents an integer from 1 to 5, c represents an integer from 2 to 20, and d represents an integer from 0 to 20;

(D) a powder that is surface-treated with an N-acylamino acid and a methylpolysiloxane;

(E) 0.1 to 1% by mass of dextrin palmitate; and wherein said cosmetic does not comprise an organically modified clay mineral.

2. The water-in-oil emulsion cosmetic, according to claim 1, wherein:

said (A) polar oil that is liquid at 25° C. and having an IOB value greater than 0.1 is at least one polar oil selected from the group consisting of oleic acid, isostearic acid, isopropyl myristate, octyl palmitate, isopropyl palmitate, butyl stearate, hexyl laurate, myristyl myristate, decyl oleate, isononyl isononanoate, isotridecyl isononanoate, cetyl ethylhexanoate, glycol distearate, glyceryl diisostearate, neopentyl glycol dicaprate, diisostearyl malate, trimethylolpropane triisostearate, glyceryl tri-2-ethylhexanoate (triethylhexanoin), trimethylolpropane trioctanoate, trimethylolpropane triisostearate, diisobutyl adipate, N-lauryol-L-glutamic acid-2-octyldodecyl ester, 2-hexyldecyl adipate, diisopropyl sebacate, ethylhexyl methoxycinnamate, olive oil, castor oil, decyltetradecanol, octyldodecanol, and oleyl alcohol.

3. The water-in-oil emulsion cosmetic, according to claim 1, wherein:

said (A) polar oil that is liquid at 25° C. and having an IOB value greater than 0.1 is at least one polar oil selected from the group consisting of isostearic acid, myristyl myristate, decyl oleate, isotridecyl isononanoate, cetyl ethylhexanoate, glycol distearate, glyceryl diisostearate, neopentyl glycol dicaprate, trimethylolpropane triisostearate, glyceryl tri-2-ethylhexanoate (triethylhexanoin), trimethylolpropane trioctanoate, trimethylolpropane triisostearate, diisobutyl adipate, N-lauryol-L-glutamic acid-2-octyldodecyl ester, 2-hexyldecyl adipate, diisopropyl sebacate, ethylhexyl methoxycinnamate, and decyltetradecanol.

* * * * *